United States Patent [19]

Meisel et al.

[11] Patent Number: 5,130,442
[45] Date of Patent: Jul. 14, 1992

[54] CHROMOGENIC ENAMINE COMPOUNDS, THEIR PREPARATION AND USE AS COLOR FORMERS

[75] Inventors: Karlheinrich Meisel, Odenthal-Osenau; Hubertus Psaar, Leverkusen, both of Fed. Rep. of Germany

[73] Assignee: Bayer Aktiengesellschaft, Leverkusen, Fed. Rep. of Germany

[21] Appl. No.: 606,410

[22] Filed: Oct. 31, 1990

[30] Foreign Application Priority Data

Dec. 7, 1989 [DE] Fed. Rep. of Germany ....... 3940480

[51] Int. Cl.⁵ ............................................. C07D 209/04
[52] U.S. Cl. .................................... 548/411; 548/409; 546/15; 546/18
[58] Field of Search .................. 548/409, 411; 546/15, 546/18

[56] References Cited

U.S. PATENT DOCUMENTS

| | | | |
|---|---|---|---|
| 3,872,023 | 3/1975 | Baum et al. | 428/402.22 |
| 4,153,609 | 5/1979 | Petitpierre et al. | 548/463 |
| 4,238,562 | 12/1980 | Ishida et al. | 548/409 |
| 4,252,975 | 2/1981 | Petitpierre et al. | 544/62 |
| 4,295,663 | 10/1981 | Petitpierre et al. | 503/217 |

FOREIGN PATENT DOCUMENTS

| | | |
|---|---|---|
| 2119933 | 11/1972 | Fed. Rep. of Germany . |
| 2700937 | 7/1977 | Fed. Rep. of Germany . |
| 3247488 | 7/1983 | Fed. Rep. of Germany . |
| 3337296 | 4/1985 | Fed. Rep. of Germany . |
| 2379382 | 9/1978 | France . |
| 2491638 | 4/1982 | France . |
| 1053905 | 1/1967 | United Kingdom . |
| 2113860 | 3/1969 | United Kingdom . |

OTHER PUBLICATIONS

Chemical Abstracts, vol. 82, No. 4, Jan. 27, 1975, Abstract No. 18620E, p. 111.

*Primary Examiner*—Mukund J. Shah
*Assistant Examiner*—Y. N. Gupta
*Attorney, Agent, or Firm*—Sprung Horn Kramer & Woods

[57] ABSTRACT

Compounds of the formula

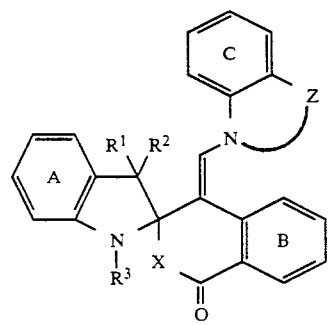

in which
$R^1/R^2$ are alkyl, cycloalkyl, aralkyl or alkylene,
$R^3$ is alkyl, cycloalkyl or aralkyl,
Z is alkylene,
X is O or are highly suitable as color formers in recording materials based on acid developers. They give yellow or orange hues which have excellent sublimation and light fastness.

7 Claims, No Drawings

CHROMOGENIC ENAMINE COMPOUNDS, THEIR PREPARATION AND USE AS COLOR FORMERS

The present invention relates to chromogenic enamine compounds, processes for their preparation and their use in pressure- and heat-sensitive recording materials.

The new compounds have the general formula

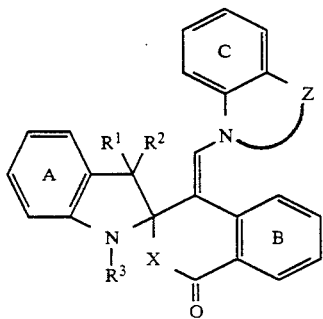

in which
R$^1$ and R$^2$, independently of one another, are alkyl, cycloalkyl, aralkyl or together are an alkylene bridge,
R$^3$ is alkyl, cycloalkyl or aralkyl,
Z is an alkylene bridge, which may be further substituted or together with the nitrogen and a further hetero atom forms a 5- or 6-membered ring, and
X is oxygen or NR$^4$,
R$^4$ is hydrogen, alkyl, aryl, aralkyl, alkylcarbonyl, aralkylcarbonyl, alkylsulphonyl, aralkylsulphonyl or arylsulphonyl and
the rings A, B and C and the radicals mentioned in turn can carry nonionic substituents customary in dyestuff chemistry.

Examples of nonionic substituents customary in dyestuff chemistry are halogen, hydroxyl, alkoxy, aryloxy, aralkoxy, heteryloxy, aryl, heteryl, alkylmercapto, arylmercapto, aralkylmercapto, alkylsulphonyl, cyano, carbamoyl, alkoxycarbonyl, amino, which can be substituted by 1 or 2 alkyl, aryl or aralkyl groups or the substituents of which can be ring-closed, alkenyloxy, alkylcarbonyloxy, arylcarbonyloxy and, as substituents of the rings, also alkyl, aralkyl, nitro or arylvinyl.

Alkyl preferably represents C$_1$-C$_{30}$-alkyl, in particular C$_1$-C$_{12}$-alkyl and very particularly C$_1$-C$_4$-alkyl, and alkenyl preferably represents C$_2$-C$_5$-alkenyl.

Suitable alkylene bridges R$^1$/R$^5$ have 5 or 6 C atoms, while alkylene bridges Z preferably contain 2 to 3 C atoms in the chain.

Halogen is understood to represent fluorine, bromine and in particular chlorine.

The alkyl radicals and the alkyl radicals in the alkoxy, alkylthio, dialkylamino, alkanoylamino, alkylsulphonyl and alkoxycarbonyl groups can be branched and substituted, for example, by fluorine, chlorine, C$_1$-C$_4$-alkoxy, cyano or C$_1$-C$_4$-alkoxycarbonyl. Specific examples are methyl, ethyl, propyl, 2-propyl, 2,2-dimethylpropyl, 2-butyl, 1-hexyl, 1-octyl, 1-dodecyl, 1-tetradecyl, 1-hexadecyl, 1-octadecyl, 2-bornylmethyl, 2-chloroethyl, 2-cyanoethyl, 2-methoxyethyl, 2-ethoxycarbonylethyl, trifluoromethyl.

Cycloalkyl is in particular understood to represent cyclohexyl, aryl to represent phenyl and naphthyl, aralkyl to represent benzyl and phenethyl, heteryl to represent pyridyl, pyrimidyl, pyrazinyl, triazinyl, imidazolyl, oxazolyl, thiazolyl, triazolyl, thiadiazolyl or tetrazolyl, which can be benzo-fused, and hetaralkyl to represent the rings or ring systems mentioned, which are linked to nitrogen via methylene or ethylene. The rings can be substituted by nonionic substituents, in particular by C$_1$-C$_4$-alkyl, C$_1$-C$_4$-alkoxy, cyano, nitro or halogen.

Specific examples of substituted phenyl radicals are 2-, 3- or 4-tolyl, 2-, 3- or 4-anisyl, 2-, 3- or 4-chlorophenyl, 2-, 3- or 4-nitrophenyl, 2-, 3- or 4-cyanophenyl, 2-, 3- or 4-ethoxycarbonylphenyl, 2-, 3- or 4-methoxysulphonylphenyl, 2-, 3- or 4-trifluoromethylphenyl, 2,3-dinitrophenyl, 3,4-dimethylphenyl, 2-chloro-4-nitrophenyl,3-chloro-4-nitrophenyl,5-chloro-2-methyl-4-nitrophenyl, 4-chloro-3-methylphenyl, 3-chloro-4-methoxyphenyl, 3-chloro-4-trifluoromethylphenyl, 3,4-dicyanophenyl, 2,5-dichloro-4-cyanophenyl, 2-methyl-1-naphthyl.

Of particular interest are compounds of the general formula

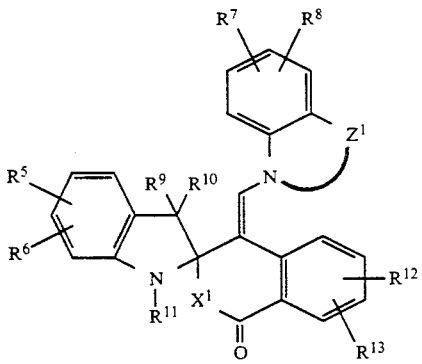

in which—independently of one another—
R$^5$, R$^6$, R$^7$, R$^8$, R$^{12}$, R$^{13}$ are hydrogen, C$_1$-C$_{18}$-alkyl, which can be unsubstituted or substituted by hydroxyl, C$_1$-C$_8$-alkoxy, cyano, carboxamido, chlorine or bromine, phenyl, which can be unsubstituted or substituted by halogen, C$_1$-C$_4$-alkyl, C$_1$-C$_4$-alkoxy, phenyl-C$_1$-C$_4$-alkyl, halogen, C$_1$-C$_{18}$-alkoxy, phenoxy, carboxyl, C$_1$-C$_{18}$-alkoxycarbonyl, C$_1$-C$_{18}$-alkylsulphonyl, cyano, hydroxyl, C$_1$-C$_{18}$-alkylcarbonyl, C$_1$-C$_{18}$-alkylcarbonyloxy, C$_1$-C$_{18}$-alkylamino, C$_1$-C$_{18}$-dialkylamino, C$_1$-C$_{18}$-N-alkyl-N-phenylamino, phenylamino, C$_1$-C$_{18}$-alkylcarbonylamino, cyano, nitro or R$^5$ and R$^6$ and R$^7$ and R$^8$ represent a further fused benzene ring, R$^9$ and R$^{10}$ represent C$_1$-C$_{18}$-alkyl, C$_5$- or C$_6$-cycloalkyl, benzyl or together C$_5$- or C$_6$-alkylene, which can be unsubstituted or further substituted, R$^{11}$ represents C$_1$-C$_{18}$-alkyl, benzyl, phenethyl, which can be unsubstituted or further substituted, Z$^1$ represents a C$_2$- or C$_3$-alkylene bridge, which can be unsubstituted or further substituted, or together with the nitrogen and a further hetero atom forms a 5- or 6-membered ring, X$^1$ represents oxygen or NR$^{14}$, in which R$^{14}$ represents hydrogen, C$_1$-C$_{18}$-alkyl, phenyl, C$_1$-C$_4$-aralkyl, C$_1$-C$_{18}$C -alkylcarbonyl, C$_1$-C$_4$-aralkylcarbonyl, C$_1$-C$_{18}$-alkylsulphonyl, C$_1$-C$_4$- aralkylsulphonyl, which can be unsubstituted or further substituted.

It goes without saying that the large number of substituents are selected in such a manner that low-cost products of optimum efficiency in industrial application are formed. Thus, it is, for example, not recommended for more than 2 long-chain (i.e. containing more than 4 C atoms) alkyl radicals to be contained in a colour former molecule. Rather, the chain length selected should be such that a product is formed which has good solubility in the application medium.

Compounds of the general formula

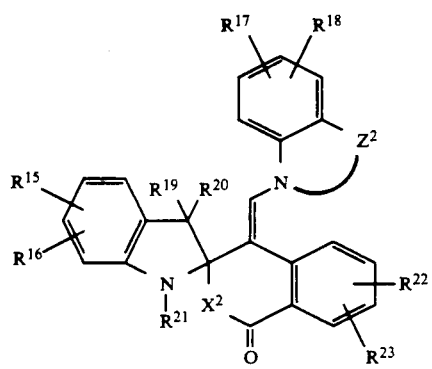

III in which—independently of one another—
$R^{15}$, $R^{16}$, $R^{17}$, $R^{18}$ are hydrogen, $C_1$–$C_8$-alkyl, phenyl, chlorine, bromine, $C_1$–$C_4$-alkoxycarbonyl, $C_1$–$C_4$-alkoxy, cyano or nitro,
$R^{19}$ and $R^{20}$ are $C_1$–$C_4$-alkyl, $C_5$- or $C_6$-cycloalkyl, benzyl or together a $C_5$- or $C_6$-alkylene bridge,
$R^{21}$ is $C_1$–$C_8$-alkyl, benzyl, phenethyl, cyanoethyl, amidoethyl, $C_1$–$C_4$-alkoxyethyl, $C_1$–$C_4$-halogenoalkyl or $C_1$–$C_4$-hydroxyalkyl,
$Z^2$ is a $C_2$- or $C_3$-alkylene bridge, which can be unsubstituted or substituted by methyl groups, or
$Z^2$ together with the nitrogen and a further NH or O atom forms a 5- or 6-membered ring, which can be unsubstituted or substituted by $C_1$–$C_4$-alkyl groups, halogen or $C_1$–$C_4$-alkoxy groups,
$R^{22}$ and $R^{23}$ are hydrogen, $C_1$–$C_4$-alkyl, chlorine, bromine or $C_1$–$C_4$-alkoxy,
$X^2$ is oxygen or $NR^{24}$, in which
$R^{24}$ can be hydrogen, $C_1$–$C_{18}$-alkyl, phenyl, $C_1$–$C_4$-alkoxyphenyl, 4-chlorophenyl, 2-, 3- or 4-tolyl, benzyl, phenylethyl, $C_1$–$C_{18}$-alkylcarbonyl, phenyl-$C_1$–$C_4$-alkylcarbonyl or $C_1$–$C_{18}$-alkylsulphonyl are also of particular interest.

Of these, in particular compounds of the general formula

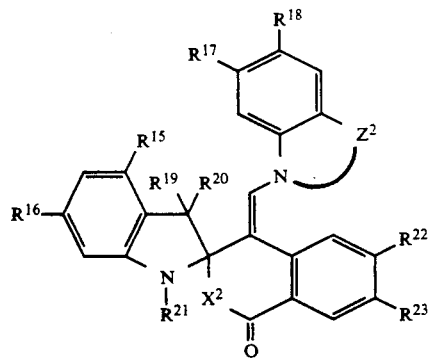

IV in which
$R^{15}$ to $R^{23}$, $X^2$ and $Z^2$ have the abovementioned meaning, and compounds of general formula

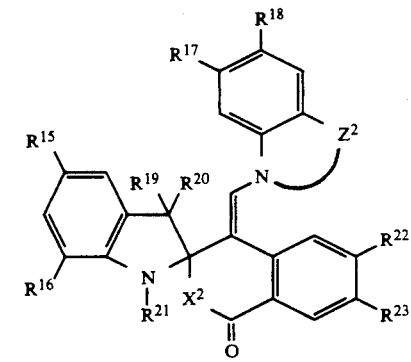

V in which $R^{15}$ to $R^{23}$, $X^2$ and $Z^2$ have the abovementioned meaning, are of particular interest.

Compounds of the general formula

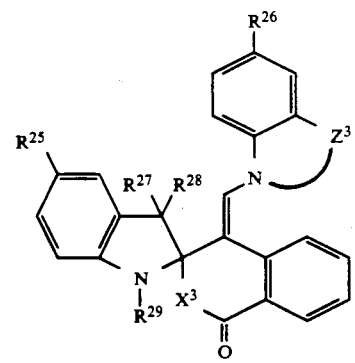

VI in which—independently of one another—
$R^{25}$ and $R^{26}$ are hydrogen, $C_1$–$C_4$-alkyl, $C_1$–$C_4$-alkoxy, chlorine, cyano, nitro or $C_1$–$C_4$-alkoxycarbonyl,
$X^3$ is oxygen or $NR^{27}$,
$R^{27}$ is hydrogen, $C_1$–$C_8$-alkyl, which can be straight-chain or branched, benzyl or phenethyl and
$Z^3$ represents a —$C_2$— or —$C_3$-alkylene bridge, each of which can be substituted by methyl groups,
are of very particular interest.

The invention further relates to a process for the preparation of compounds of the formula I, which process is characterized in that compounds of the formula

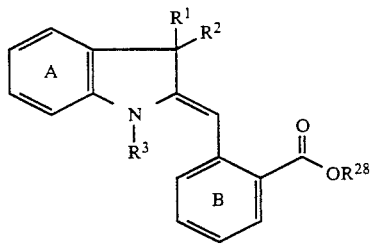

VII in which
A, B, $R^1$ to $R^3$ have the abovementioned meaning and
$R^{28}$ represents $C_1-C_4$-alkyl which is preferably substituted by electron-withdrawing groups, such as, for example, CN or $COOC_1-C_4$-alkyl, or phenyl which is unsubstituted or substituted by $C_1-C_4$-alkyl, chlorine, nitro, cyano or $C_1-C_4$-alkoxy,
are condensed with compounds of the general formula

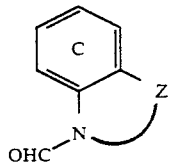

VIII in which C and Z have the abovementioned meaning, in the presence of a dehydrating agent or reacted with compounds of the general formula

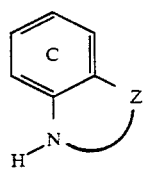

IX in which C and Z have the abovementioned meaning, in the presence of a $C_1-C_4$-alkyl orthoformate in an inert solvent or an organic acid, in particular acetate acid, and the resulting dyestuffs of the formula

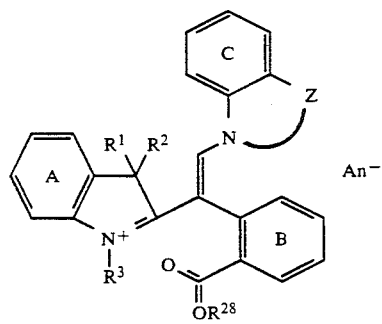

X in which
$R^1-R^3$, Z, A, B and C have the abovementioned meaning and
$An^-$ represents an anion, are cyclized to give the products of the general formula I, the cyclization being carried out either in an aqueous or non-aqueous medium by adding a base.

Examples of anions $An^-$ are $Cl^-$, $Br^-$, $I^-$, $BF_4^-$, $ClO_4^-$, $HSO_4^-$, $SO_4^{2-}$, $SiF_6^{2-}$, $PF_6^-$, $H_2PO_4^-$, $PO_4^{3-}$, or the anions of $C_1-C_{18}$-carboxylic acids, $C_2-C_{18}$-dicarboxylic acids, $C_1-C_{18}$-alkylsulphonic acids, benzene- or naphthalene- mono- or -dicarboxylic or -sulphonic acids, which are unsubstituted or substituted by halogen, $C_1-C_4$-alkyl, $C_1-C_4$-alkoxy, hydroxyl, cyano, $C_1-C_4$-alkoxycarbonyl, nitro or $C_1-C_4$-alkylsulphonyl.

The reaction of the compounds VII and VIII is usually carried out using dehydrating reagents in the absence of or even in the presence of solvents which are inert under these conditions at temperatures between 0° C. and the boiling point of the particular medium. If appropriate, after the inert solvent has been removed, the reaction product is then poured into, for example, water or an alcohol.

Examples of dehydrating reagents are phosphorus oxychloride, phosphorus pentachloride, disphosphorus pentoxide, phosgene, phosphorus trichloride, phosphorus tribromide, sulphuryl chloride, thionyl chloride, oxalyl chloride or mixtures thereof. Preferably, phosphoryl chloride and phosphorus oxychloride/diphosphorus pentoxide are used.

Examples of inert solvents which are suitable for the reaction of VII and VIII or VII and IX are toluene, chlorobenzene, dichlorobenzene, nitrobenzene, chlorinated aliphatic hydrocarbons, such as 1,2-dichloroethane.

The compounds of the general formula VII are obtained by reacting 2-methyleneindoline compounds of the general formula

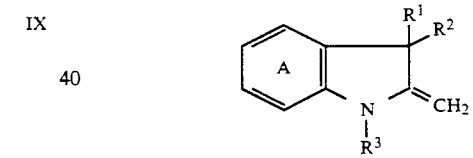

XI with o-halogenobenzoic acids of the general formula

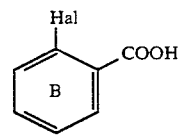

XII in which the radicals mentioned have the meaning described above and Hal preferably represents chlorine, bromine or iodine, and esterifying the resulting products by methods known from the literature.

This reaction is preferably carried out in an aqueous medium at pH values between 4 and 11, in particular between 7 and 9, and at temperatures between 60° C. and the boiling point of the reaction medium, in general at ~100° C.

Cu powder, CuCl and KI, each by itself or in a mixture, has proven suitable as catalysts. The reaction times are in general between 1 and 48 hours.

Examples of suitable components of the general formula XI are: 1,3,3-trimethyl-2-methyleneindoline, 1-ethyl-3,3-dimethyl-2-methyleneindoline, 1-cyanoethyl-3,3-dimethyl-2-methyleneindoline, 1-carboamidoethyl- 3,3-dimethyl-2-methyleneindoline, 1-(2-hydroxyethyl)-3,3-dimethyl-2-methyleneindoline, 1-(2-chloroethyl)-3,3-dimethyl-2-methyleneindoline, 1-octadecyl-3,3-dimethyl-2-methyleneindoline, 1-octyl-3,3-dimethyl-2-methyleneindoline, 1,3,3-trimethyl-2-methylene-5-chloroindoline, 1,3,3-trimethyl-2-methylene-5-methoxycarbonylindoline, 1,3,3-trimethyl-2-methylene-5-butoxycarbonylindoline, 1,3,3-trimethyl-2-methylene-5-octadecyloxycarbonylindoline, 1,3-dimethyl-3-ethyl-2-methyleneindoline, 1,3-dimethyl-3-octadecyl-2-methyleneindoline, 1,3-dimethyl-3-isopropyl-2-methyleneindoline, 1,3,3,4-tetramethyl-2-methyleneindoline, 1,3,3,5-tetramethyl-2-methyleneindoline, 1,3,3,6-tetramethyl-2-methyleneindoline, 1,3,3,7-tetramethyl-2-methyleneindoline or isomeric mixtures of these compounds, 1,3,3-trimethyl-5-octyl-2-methyleneindoline, 1,3,3-trimethyl-5-dodecyl-2-methyleneindoline, 1,3,3-trimethyl-5-octadecyl-2-methyleneindoline, 1,3,3-trimethyl-4,5-benzo-2-methyleneindoline, 1,3,3-trimethyl-5,6-benzo-2-methyleneindoline, 1,3,3-trimethyl-6,7-benzo-2-methyleneindoline, 1,3,3-trimethyl-2-methylene-5-methoxyindoline, 1,3,3-trimethyl-2-methylene-5-butoxyindoline, 1,3,3-trimethyl-2-methylene-5-octyloxyindoline, 1,3,3-trimethyl-2-methylene-5-phenylindoline, 1,3,3-trimethyl-2-methylene-5-phenoxyindoline, 1,3,3-trimethyl-2-methylene-5-methylsulphonylindoline, 1,3,3-trimethyl-2-methylene-5-cyanoindoline, 1,3,3-trimethyl-2-methylene-5-methylcarbonylindoline, 1,3,3-trimethyl-2-methylene-5-octylcarbonylindoline, 1,3,3-trimethyl-2-methylene-5-dimethylaminoindoline, 1,3,3-trimethyl-2-methylene-5-anilinoindoline, 1,3,3-trimethyl-2-methylene-5-methylphenylaminoindoline, 1,3,3-trimethyl-2-methylene-5-acetaminoindoline.

Components of the general formula XII can be, for example: o-chlorobenzoic acid, 2,4-dichlorobenzoic acid, 2,4,6-trichlorobenzoic acid, 2-chloro-4-methylbenzoic acid, 2-chloro-4,6-dimethylbenzoic acid, 2-chloro-4-nitrobenzoic acid, 2-chloro-5-nitrobenzoic acid, 2-chloro-4,5-dinitrobenzoic acid, 2-chloro-4,6-dinitrobenzoic acid.

Examples of suitable enamine end systems are: indoline, 2-methylindoline, 2,3-dimethylindoline, 2,3,3-trimethylindoline, 2-phenylindoline, tetrahydroquinoline, 2,2,4-trimethyltetrahydroquinoline, tetrahydrocarbazole, N-alkylquinoxaline, N-alkylbenzimidazoline, benzoxazoline, which can all be unsubstituted or further substituted.

Examples of suitable bases for cyclizing the colour former are alkali metal hydroxide, alkaline earth metal hydroxides, alkali metal or alkaline earth metal carbonates or alkali metal or alkaline earth metal bicarbonates, amines, such as ammonia, methylamine, ethylamine, N-propylamine, isopropylamine, N-butylamine, isobutylamine, sec.-butylamine, tert.-butylamine, N-octylamine, isooctylamine, octadecylamine or others, benzylamine, phenylethylamine, phenylbutylamine, aniline, alkoxyaniline, p-alkylaniline, dialkylaminoaniline.

The invention also relates to the use of the chromogenic enamine compounds of the formula I or mixtures thereof for printable, thermoreactive or electrochromic recording materials, the recording material containing an acid colour developer.

Suitable acid developers are in particular clays, acidic oxides or acidic salts and monomeric or polymeric phenols or carboxylic acid.

Upon contacting the colour formers with the acid developer, deep yellow or orange shades are obtained which have excellent sublimation and light fastness.

They are also valuable in a mixture with one or more other known colour formers, for example 3,3-bis-(aminophenyl)phthalides, 3,3-bis(indolyl)phthalides, 3-aminofluorans, spirodipyrans, chromenoindoles, phenoxazines, phenothiazines, carbazolylmethanes, 4,4-diaryldihydroquinazolones, benzoxazines or other triarylmethane leuko dyestuffs to give green, grey or black colorations.

The enamine compounds of the formula I have good colour intensity not only on phenolic substrates but also in particular on activated clays. They are suitable in particular as colour formers for use in a heat- or pressure-sensitive recording material, which can also be used as copying material. In general, they are distinguished by a high development rate in combination with reduced sensitivity of the recording materials to unintended premature development.

The enamine compounds of the formula I are distinguished by good light fastness and weather-ageing stability not only in the developed but also the undeveloped state.

A pressure-sensitive material consists, for example, of at least one pair of sheets containing at least one colour former of the formulae (sic) I, dissolved or dispersed in a nonvolatile organic solvent, and an acid developer.

These types of processes and preparations are disclosed, for example, in U.S. Pat. Nos. 2,800,457, 2,800,458, 2,948,753, 3,096,189 and 3,193,404 and in German Offenlegungsschriften 2,555,080 and 2,700,937.

To prevent premature activation of the colour formers present in the pressure-sensitive recording material, they are preferably enclosed in microcapsules, which, as a rule, can be broken by applying pressure.

Examples of suitable capsule wall materials are gelatin/gum arabic, polyamides, polyurethanes, polyureas, polysulphonamides, polyesters, polycarbonates, polysulphonates, polyacrylates and phenol/melamine or urea/formaldehyde condensation products, such as are described, for example, in M. Gutcho, Capsule Technology and Microencapsulation, Noyes Data Corporation 1972, G. Baster, Microencapsulation, Processes and Applications, edited by J. E. Vandegaar and in German Offenlegungsschriften 2,237,545 and 2,119,933.

In the process according to the invention, microcapsules whose shells are made of polyaddition products of polyisocyanates with polyamines are preferably used. The isocyanates to be used for preparing such microcapsules are diisocyanates, polyisocyanates, diisocyanates having biuret structure, polyisocyanates modified by di- or trifunctional alcohols or other modified isocyanates, for example those of the formula:

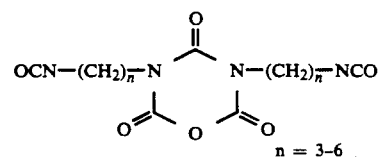

n = 3-6

Diamines which are suitable for the reaction with the isocyanates mentioned are aliphatic primary or secondary di- or polyamines.

Isocyanates, amines, solvents and a suitable preparation process for these microcapsules are described, for example, in DE-A 3,203,059. Thermoreactive recording systems comprise, for example, heat-sensitive recording and copying materials and recording and copying papers.

Such a material is described, for example, in DE-A 2,555,080.

Suitable developers are the same electron acceptors which are used in pressure-sensitive papers, preferably phenolic compounds, which are described, for example, in DE-A 1,251,348, and boric acid and organic, preferably aliphatic, dicarboxylic acids.

A further suitable thermoreactive development system is described in DE-A 3,337,296, in which acid-modified polymers, preferably of acrylonitrile, act as developer.

A further application of the compounds of the formula I-VI is the generation of a colour image by means of photo-curable microcapsules, such as are described, for example, in DE-A 3,247,488.

The enamine compounds o the formula I or the dyestuffs of the formula X formed therefrom by ring opening are suitable for colouring polyacrylonitrile, tannin-treated cotton and other acid-modified fibres, fabrics and powders.

EXAMPLE 1

191 g of o-bromobenzoic acid, 113 g of water and 148 g of 1,3,3-trimethyl-2-methyleneindoline are brought to a pH of 8 with ~105 ml of 30% strength sodium hydroxide solution, 1 g of CuCl and 2 g of Cu powder are added, and the mixture is heated at 100° C. for 12 hours. During this time, the pH is maintained at 8 by continuously adding ~89 ml of 30% strength sodium hydroxide solution via the autotitrator. The mixture is then filtered while hot, brought to a pH of 6 with sulphuric acid and filtered off with suction. The moist precipitate is boiled in 1.5 l of methanol, filtered off with suction and dried to give 184.7 g of the compound of the formula:

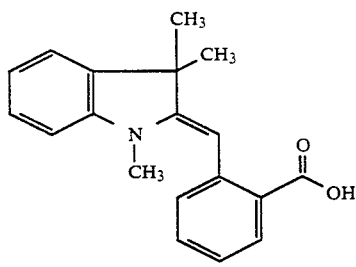

Melting point: 132°-133° C.

141 g of the intermediate 1a, 72.5 g of p-nitrophenol and 67.36 g of 4-dimethylaminopyridine are initially introduced into 800 ml of methylene chloride, and 160 g of dicyclohexylcarbodiimide are added. The mixture is stirred at room temperature for 24 hours and the product is filtered off. The mother liquor is extracted twice with 1 l each of 5% strength acetic acid and 1 l of water and evaporated on a rotary evaporator. The residue is recrystallized from cyclohexane to give 188 g of the compound of the formula

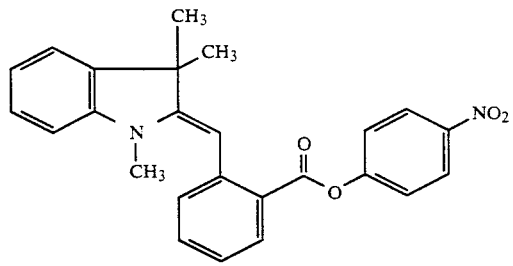

of melting point 125°-126° C.

10.32 g of the intermediate 1b are stirred into a solution of 4.025 of N-formyl-2-methylindoline in 50 ml of phosphorus oxychloride, and the mixture is stirred at room temperature for 12 hours. The batch is poured into 500 ml of water and, after stirring for another 24 hours, the dyestuff of the formula

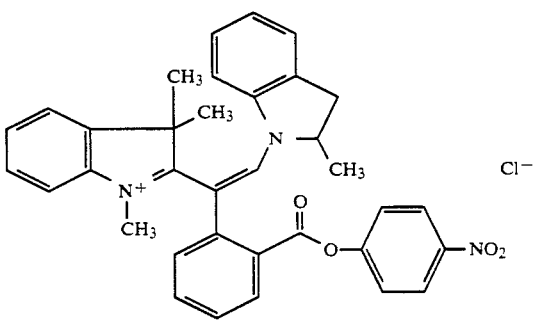

crystallizes. It is filtered off with suction and washed until neutral. The moist precipitate is dissolved in 100 ml of dimethylformamide, 50% strength sodium hydroxide solution is added, and the mixture is stirred at room temperature. After 1-2 hours, a colourless precipitate is formed which has the following structure:

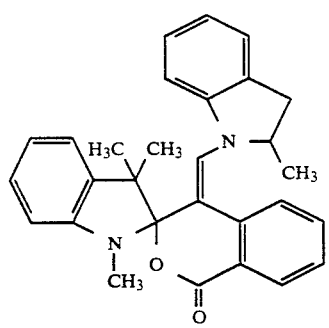

Yield: 2.5 g, $\lambda_{max}$ (in glacial acetic acid): 434 nm.

EXAMPLE 2

The procedure of Example 1 is repeated, except that the intermediate 1b described in Example 1 is reacted with 4.025 g of N-formyltetrahydroquinoline instead of N-formyl-2-methylindoline, to give likewise a valuable colour former which develops a yellow colour on acid clay ($\lambda_{max}$ (in glacial acetic acid)=432 nm).

EXAMPLE 3

The procedure of Example 1 is repeated, except that the intermediate 1b described in Example 1 is reacted with 5.075 g of N-formyl-2,2,4-trimethyltetrahydroquinoline instead of N-formyl-2-methylindoline, to give likewise a valuable colour former which develops a yellow colour on acid clay ($\lambda_{max}$ (in glacial acetic acid)=431 nm).

EXAMPLE 4

117.2 g of the intermediate 1a described in Example 1 are dissolved in 400 ml of chlorobenzene and 192 g of 10% strength sodium hydroxide solution, 1 g of hexadecyltrimethylammonium bromide is added, and the esterificatioin is carried out at 40° C. using 72 g of dimethyl sulphate. After stirring overnight, the organic phase is separated off, washed three times with water and evaporated on a rotary evaporator to give 111.1 g of a yellow oil of the formula

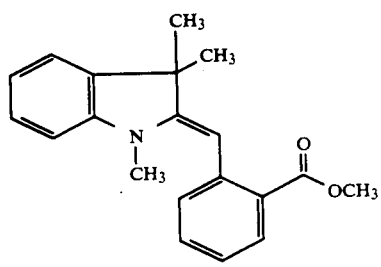

4a

This intermediate is further reacted in accordance with the procedure described in Example 1 to give likewise the colour former of Example 1.

EXAMPLE 5

29.4 g of the intermediate 1a described in Example 1 are heated together with 21.4 g of diphenyl carbonate and 1 g of sodium carbonate at 140° C. for 5 hours. The cooled batch is taken up in chloroform, extracted with NaOH and evaporated on a rotary evaporator in vacuo to give 22.4 g of the compound of the formula

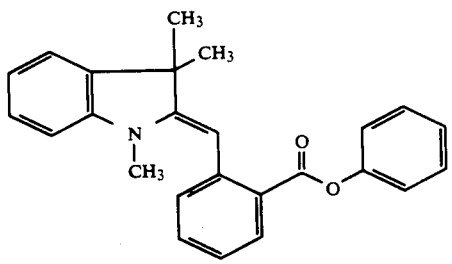

5a

This intermediate is further reacted in accordance with the procedure described in Example 1 to give likewise the colour former of Example 1.

Analogously, the colour former of Examples 2 and 3 can be obtained from the intermediate 5a.

EXAMPLE 6

The procedure of Example 1 is repeated, using an equimolar amount of 1,3,3-trimethyl-2-methylene-5-chloroindoline instead of the 1,3,3-trimethyl-2-methyleneindoline described in Example 1, to give a further valuable colour former which develops a yellow colour on acid clay ($\lambda_{max}$ (in glacial acetic acid)=406 nm).

EXAMPLE 7

If an equimolar amount of 1,3,3-trimethyl-2-methylene-5-methoxycarbonylindoline is used instead of the 1,3,3-trimethyl-2-methyleneindoline described in Example 1, the intermediate of the formula:

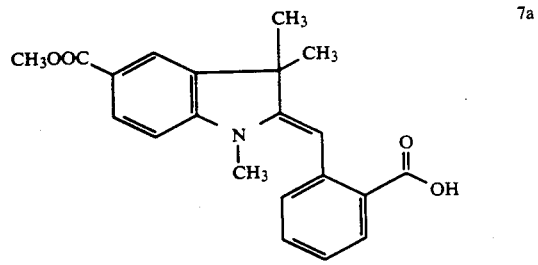

7a is obtained in the first step. Analogously to Example 1 or 5, it can be further reacted to give a colour former which develops a yellow colour on acid clay and has a $\lambda_{max}$ at 440 nm in glacial acetic acid.

EXAMPLE 8

An equally valuable colour former is obtained by further reacting the intermediate 7a of Example 7 by the method described in Example 1 or 5, but using an equimolar amount of N-formyltetrahydroquinoline instead of N-formyl-1,3,3-trimethyl-2-indoline ($\lambda_{max}$ (in glacial acetic acid)=438 nm).

EXAMPLE 9

14 g of the intermediate 1c obtained in Example 1 are introduced into 100 ml of n-butylamine and stirred at room temperature for 1 hour. The batch is poured into 1 l of water. The precipitated resin is dissolved in 50 ml of methanol and added dropwise to a solution of 50 ml of concentrated sodium hydroxide solution in 1 l of water. The colourless precipitate is filtered off with suction, washed until neutral and dried to give 6.9 g of a compound of the formula:

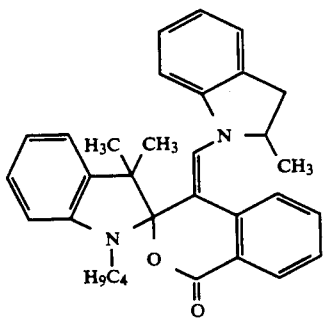

9a $\lambda_{max}$ (in glacial acetic acid)=439 nm).

The compounds of the general formula 10 are prepared analogously:

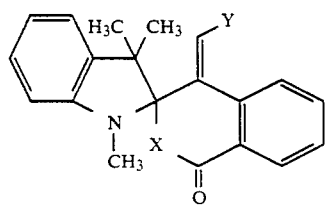

After the reaction with water-immiscible amines, the mixture is first poured into dilute hydrochloric acid, and the precipitated dyestuff is cyclized by the method described in Example 1 to give the colour former.

| Example | X | Y | (glacial acetic acid) max |
|---|---|---|---|
| 10 | i-C$_4$H$_9$—N(—)(—) | N-methyl-2-methylindoline | 438 nm |
| 11 | PhCH$_2$—N(—)(—) | | 439 nm |
| 12 | Ph(CH$_2$)$_2$—N(—)(—) | | 439 nm |
| 13 | Ph—N(—)(—) | | 439 nm |
| 14 | HN(—)(—) | 1,2,2,4-tetramethyl-1,2,3,4-tetrahydroquinoline | 426 nm |
| 15 | H$_5$C$_2$—N(—)(—) | | 426 nm |
| 16 | n-C$_4$H$_9$—N(—)(—) | | 425 nm |
| 17 | i-C$_4$H$_9$—N(—)(—) | | 425 nm |
| 18 | Ph(CH$_2$)$_2$—N(—)(—) | | 423 nm |
| 19 | PhCH$_2$—N(—)(—) | | 423 nm |

-continued

| Example | X | Y | (glacial acetic acid) max |
|---|---|---|---|
| 20 | n-C₄H₉—N(CH₃)₂ | 1-methyl-1,2,3,4-tetrahydroquinoline | 433 nm |
| 21 | i-C₄H₉—N(CH₃)₂ | | 433 nm |
| 22 | PhCH₂—N(CH₃)₂ | | 434 nm |
| 23 | Ph(CH₂)₂—N(CH₃)₂ | | 434 nm |
| 24 | n-C₄H₉—N(CH₃)₂ | 1,2-dimethyl-3,3-dimethyl-2,3-dihydroindole | 438 nm |
| 25 | i-C₄H₉—N(CH₃)₂ | | 436 nm |
| 26 | PhCH₂—N(CH₃)₂ | | 439 nm |
| 27 | Ph(CH₂)₂—N(CH₃)₂ | | 438 nm |
| 28 | n-C₄H₉—N(CH₃)₂ | 1,2-dimethyl-3,3-dimethyl-6-methoxy-2,3-dihydroindole | 451 nm |
| 29 | PhCH₂—N(CH₃)₂ | | 452 nm |
| 30 | Ph(CH₂)₂—N(CH₃)₂ | | 452 nm |
| 31 | H₅C₂—N(CH₃)₂ | 1,2-dimethyl-2,3-dihydroindole | 439 nm |

| Example | X | Y | (glacial acetic acid) max |
|---|---|---|---|
| 32 | H₃C—N⟨ | | 439 nm |
| 33 | n-C₄H₉—N⟨ | | 439 nm |
| 34 | HN⟨ | | 439 nm |
| 35 | HN⟨ | tetrahydroquinoline | 433 nm |
| 36 | HN⟨ | indoline | 436 nm |
| 37 | H₃C—N⟨ | | 436 nm |
| 38 | H₅C₂—N⟨ | | 436 nm |

EXAMPLE 39

Production of a Pressure-sensitive No-carbon Copying Paper

A solution of 3 g of the enamine compound of Example 1 in 80 g of diisopropylnaphthalene and 17 g of kerosene is microencapsulated in a manner known per se with gelatin and gum arabic by coacervation, mixed with starch solution and applied to a sheet of paper. A second sheet of paper is coated on the front with acid-activated bentonite as colour developer. The first sheet and the sheet coated with colour developer are placed with the coated sides on top of each other. By writing on the first sheet by hand or with a typewriter, pressure is applied, as a result of which a deep yellow copy which has excellent light fastness develops on the sheet coated with the developer.

If the paper coated with microcapsules is exposed to daylight and then the second sheet is written on, a likewise deep yellow copy as described above is obtained.

Examples of equally suitable developer substances on the commercial no-carbon copying paper are acid-activated bentonite (e.g. Copisil D4A10 from Südchemie Munich), p-tert.-butylphenol/formaldehyde condensation products (e.g. UCAR-CKWA 9870 from Union Carbide Corp.) and zinc p-alkylsalicylates.

We claim:

1. Compounds of the general formula

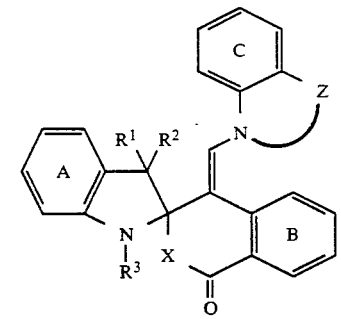

in which $R^1$ and $R^2$, independently of one another, are $C_1$–$C_{18}$-alkyl, which can be unsubstituted or substituted by hydroxyl, $C_1$–$C_8$-alkoxy, cyano, carboxamido, chlorine or bromine, phenyl, which can be unsubstituted or substituted by halogen, $C_1$–$C_4$-alkyl, $C_1$–$C_4$-alkoxy, phenyl-$C_1$–$C_4$-alkyl, $C_1$–$C_{18}$-alkoxy, phenoxy, carboxyl, $C_1$–$C_{18}$-alkoxycarbonyl, $C_1$–$C_{18}$-alkylsulphonyl, cyano, hydroxyl, $C_1$–$C_{18}$-alkylcarbonyl, $C_1$–$C_{18}$-alkylcarbonyloxy, $C_1$–$C_{18}$-alkylamino, $C_1$–$C_{18}$-dialkylamino, $C_1$–$C_{18}$-N-alkyl-N-phenylamino, phenylamino, $C_1$–$C_{18}$-alkylcarbonylamino, cyano, nitro or together are an alkylene bridge, $R^3$ is $C_1-C_{18}$-alkyl, which can be unsubstituted or substituted by hydroxyl, $C_1-C_8$-alkoxy, cyano, carboxamido, chlorine or bromine, phenyl, which can be unsubstituted or substituted by halogen, $C_1-C_4$-alkyl, $C_1-C_4$-alkoxy, phenyl-$C_1-C_4$-alkyl, $C_1-C_{18}$-alkoxy, phenoxy, carboxyl, $C_1-C_{18}$-alkoxycarbonyl, $C_1-C_{18}$-alkylsulphonyl, cyano, hydroxyl, $C_1-C_{18}$-alkylcarbonyl, $C_1-C_{18}$-alkylcarbonyloxy, $C_1-C_{18}$-alkylamino, $C_1-C_{18}$-dialkylamino, $C_1-C_{18}$-N-alkyl-N-phenylamino, phenylamino, $C_1-C_{18}$-alkylcarbonylamino, cyano, nitro, Z is a $C_2$- or $C_3$-alkylene bridge, which can be unsubstituted or substituted by methyl groups, or Z together with the nitrogen forms a 5- or 6-membered ring, which can be unsubstituted or substituted by $C_1-C_4$-alkoxy groups, halogen or $C_1-C_4$-alkoxy groups, and X is oxygen or substituted by hydroxyl, $C_1-C_8$-alkoxy, cyano, carboxamido, chlorine or bromine, phenyl, which can be unsubstituted or substituted by halogen, $C_1-C_4$-alkyl, $C_1-C_4$-alkoxy, phenyl-$C_1-C_4$-alkyl, $C_1-C_{18}$-alkoxy, phenoxy, carboxyl, $C_1-C_{18}$-alkoxycarbonyl, $C_1-C_{18}$-alkylsulphonyl, cyano, hydroxyl, $C_1-C_{18}$-alkylcarbonyl, $C_1-C_{18}$-alkylcarbonyloxy, $C_1-C_{18}$-alkylamino, $C_1-C_{18}$-dialkylamino, $C_1-C_{18}$-N-alkyl-N-phenylamino, phenylamino, $C_1-C_{18}$-alkylcarbonylamino, cyano, nitro, alkylcarbonyl, aralkylcarbonyl, alkylsulphonyl, aralkylsulphonyl or arylsulphonyl and the rings A, B and C and the radicals mentioned in turn can carry nonionic substituents, and the cationic dyestuffs which can be derived therefrom by ring opening.

2. Compounds of the general formula

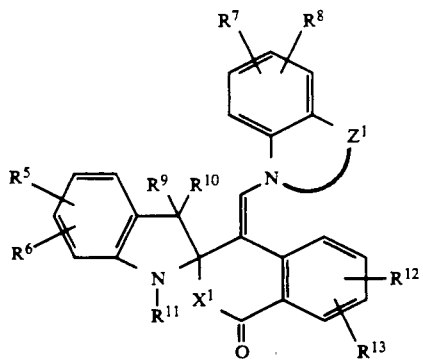

in which—independently of one another—

$R^5$, $R^6$, $R^7$, $R^8$, $R^{12}$, $R^{13}$ are hydrogen, $C_1-C_{18}$-alkyl, which can be unsubstituted or substituted by hydroxyl, $C_1-C_8$-alkoxy, cyano, carboxamido, chlorine or bromine, phenyl, which can be unsubstituted or substituted by halogen, $C_1-C_4$-alkyl, $C_1-C_4$-alkoxy, phenyl-$C_1-C_4$-alkyl, halogen, $C_1-C_{18}$-alkoxy, phenoxy, carboxyl, $C_1-C_{18}$-alkoxycarbonyl, $C_1-C_{18}$-alkylsulphonyl, cyano, hydroxyl, $C_1-C_{18}$-alkylcarbonyl, $C_1-C_{18}$-alkylcarbonyloxy, $C_1-C_{18}$-alkylamino, $C_1-C_{18}$-dialkylamino, $C_1-C_{18}$-N-alkyl-N-phenylamino, phenylamino, $C_1-C_{18}$-alkylcarbonylamino, cyano, nitro or $R^5$ and $R^6$ and $R^7$ and $R^8$ represent a further fused benzene ring, $R^9$ and $R^{10}$ represent $C_1-C_{18}$-alkyl, $C_5$- or $C_6$-cycloalkyl, benzyl or together $C_5$- or $C_6$-alkylene, which can be unsubstituted or further substituted, $R^{11}$ represents $C_1-C_{18}$-alkyl, benzyl, phenethyl, which can be unsubstituted or further substituted, $Z^1$ represents a $C_2$- or $C_3$-alkylene bridge, which can be unsubstituted or further substituted, or together with the nitrogen forms a 5- or 6-membered ring, $X^1$ represents oxygen.

3. Compounds of the general formula

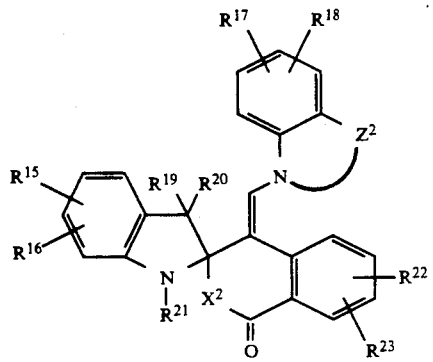

in which—independently of one another—

$R^{15}$, $R^{16}$, $R^{17}$, $R^{18}$ are hydrogen, $C_1-C_8$-alkyl, phenyl, chlorine, bromine, $C_1-C_4$-alkoxycarbonyl, $C_1-C_4$-alkoxy, cyano or nitro, $R^{19}$ and $R^{20}$ are $C_1-C_4$-alkyl, $C_5$- or $C_6$-cycloalkyl, benzyl or together a $C_5$- or $C_6$-alkylene bridge, $R^{21}$ is $C_1-C_8$-alkyl, benzyl, phenethyl, cyanoethyl, amidoethyl, $C_1-C_4$-alkoxyethyl, $C_1-C_4$-halogenoalkyl or $C_1-C_4$-hydroxyalkyl, $Z^2$ is a $C_2$- or $C_3$-alkylene bridge, which can be unsubstituted or substituted by methyl groups, or $Z^2$ together with the nitrogen forms a 5- or 6-membered ring, which can be unsubstituted or substituted by $C_1-C_4$-alkyl groups, halogen or $C_1-C_4$-alkoxy groups, $R^{22}$ and $R^{23}$ are hydrogen, $C_1-C_4$-alkyl, chlorine, bromine or $C_1-C_4$-alkoxy, $X^2$ is oxygen $R^{24}$ can be hydrogen, $C_1-C_{18}$-alkyl, phenyl, $C_1-C_4$-alkoxyphenyl, 4-chlorophenyl, 2-, 3- or 4-tolyl, benzyl, phenylethyl, $C_1-C_{18}$-alkylcarbonyl, phenyl-$C_1-C_4$-alkylcarbonyl or $C_1-C_{18}$-alkylsulphonyl.

4. Compounds of the general formula

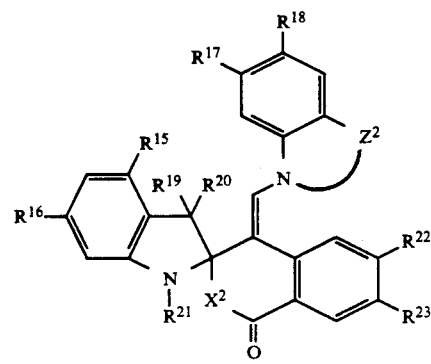

in which $R^{15}$ to $R^{23}$, $X^2$ and $Z^2$ have the meaning given in claim 3.

5. Compounds of the general formula

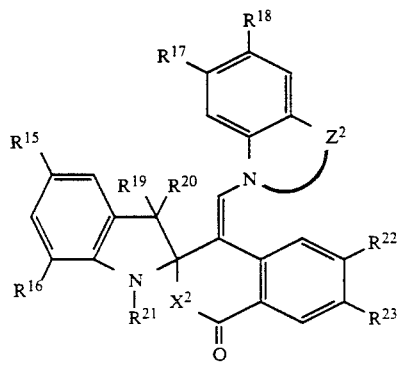

in which $R^{15}$ to $R^{23}$, $X^2$ and $Z^2$ have the meaning given in claim 3.

6. Compounds of the general formula

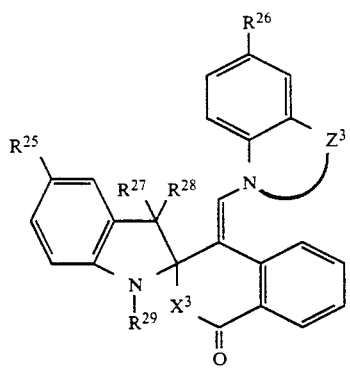

in which—independently of one another—
$R^{25}$ and $R^{26}$ are hydrogen, $C_1$–$C_4$-alkyl, $C_1$–$C_4$-alkoxy, chlorine, cyano, nitro or $C_1$–$C_4$-alkoxycarbonyl,
$X^3$ is oxygen and
$Z^3$ represents a —$C_2$— or —$C_3$-alkylene bridge, each of which can be substituted by methyl groups.

7. Compound of the formula:

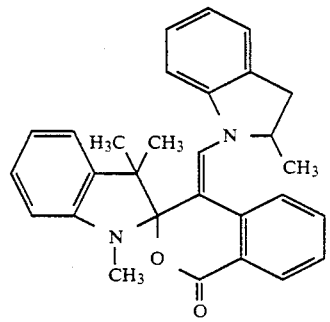

* * * * *

UNITED STATES PATENT AND TRADEMARK OFFICE
CERTIFICATE OF CORRECTION

PATENT NO. : 5,130,442
DATED : July 14, 1992
INVENTOR(S) : Meisel, et al.

It is certified that error appears in the above-indentified patent and that said Letters Patent is hereby corrected as shown below:

| | |
|---|---|
| Col. 19, line 17 | Delete " $C_1$-$C_4$-alkoxy " and substitute -- $C_1$-$C_4$-alkyl -- |
| Col. 19, lines 19-31 | Delete " or substituted by hydroxyl,.... aralkylsulphonyl or arylsulphonyl " |
| Col. 20, lines 46-50 | Delete " $R^{24}$ can be hydrogen, ....... alkylsulphonyl " |

Signed and Sealed this

Tenth Day of May, 1994

Attest:

BRUCE LEHMAN

*Attesting Officer*     *Commissioner of Patents and Trademarks*